United States Patent
Cloonan et al.

[11] Patent Number: 5,837,222
[45] Date of Patent: Nov. 17, 1998

[54] LIQUID DENTAL CLEANING SOLUTION

[76] Inventors: Richard A. Cloonan, 17750 Plaza Marlena, San Diego, Calif. 92128; Lawrence E. Towle, 14721 Caminito Orense Oeste, San Diego, Calif. 92129

[21] Appl. No.: 740,238

[22] Filed: Oct. 25, 1996

Related U.S. Application Data

[63] Continuation-in-part of Ser. No. 476,205, Jun. 7, 1995, abandoned, which is a continuation-in-part of Ser. No. 259,917, Jun. 10, 1994, Pat. No. 5,573,398.

[51] Int. Cl.[6] ................................. A61K 7/16; A61K 7/18
[52] U.S. Cl. ................................. 424/49; 424/52
[58] Field of Search ................................. 424/49, 50, 51, 424/52, 53, 54, 55, 56, 57, 58

[56] References Cited

U.S. PATENT DOCUMENTS

| | | | |
|---|---|---|---|
| 3,134,127 | 5/1964 | Klein | 15/321 |
| 3,211,149 | 10/1965 | Fono | 128/232 |
| 3,566,869 | 3/1971 | Crowson | 128/230 |
| 3,731,675 | 5/1973 | Kelly | 128/62 |
| 4,181,997 | 1/1980 | O'Rourke | 15/24 |
| 4,264,592 | 4/1981 | Xhajanka | 424/195 |
| 4,340,365 | 7/1982 | Pisanu | 433/80 |
| 4,564,519 | 1/1986 | Pellico et al. | 424/48 |
| 4,672,953 | 6/1987 | DiVito | 128/66 |
| 4,903,688 | 2/1990 | Bibby et al. | 128/66 |
| 4,991,570 | 2/1991 | Bullard | 128/66 |
| 5,137,723 | 8/1992 | Yasmamoto et al. | 424/400 |
| 5,145,367 | 9/1992 | Kasten | 433/84 |
| 5,258,173 | 11/1993 | Waterfield | 424/49 |
| 5,275,803 | 1/1994 | Dawson | 424/52 |
| 5,458,563 | 10/1995 | Stewart | 601/162 |
| 5,463,792 | 11/1995 | Hogan et al. | 15/322 |

*Primary Examiner*—Nicholas D. Lucchesi
*Attorney, Agent, or Firm*—Fitch, Even, Tabin & Flannery

[57] ABSTRACT

A dental cleaning solution is an aqueous solution of sodium fluoride in water, from 0.25 to 8 ppm; sodium tripolyphosphates from 100 to 1000 mg per gallon of water; disodium edetate from 0.01 to 0.5 cc per gallon of water; and a detergent from 1 to 10 cc per gallon of water.

24 Claims, 6 Drawing Sheets

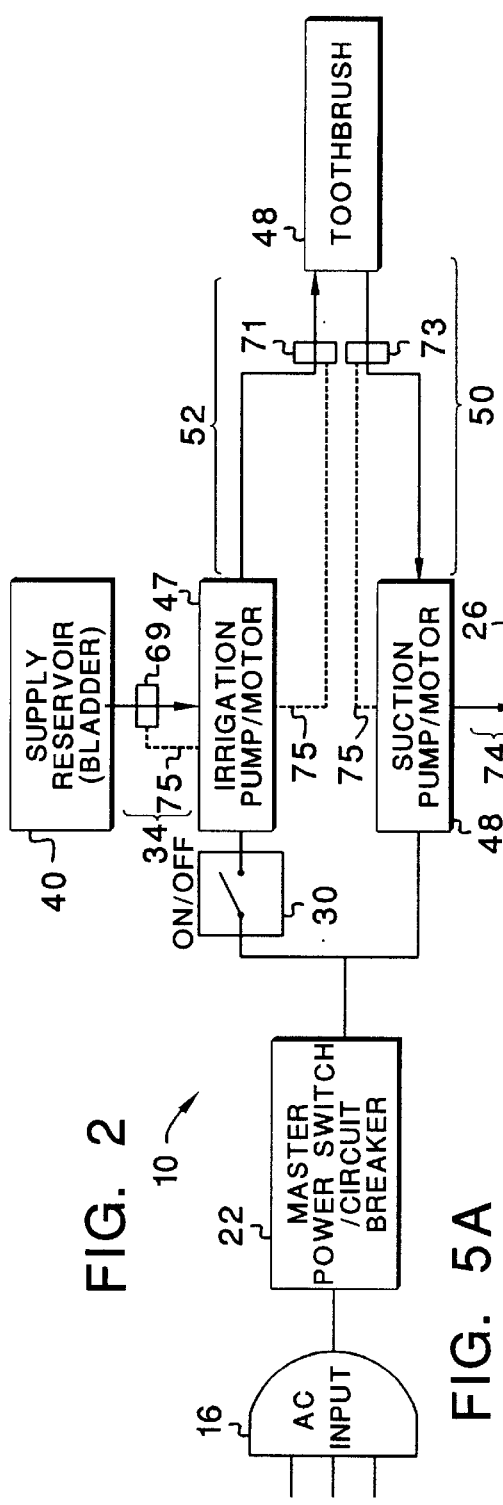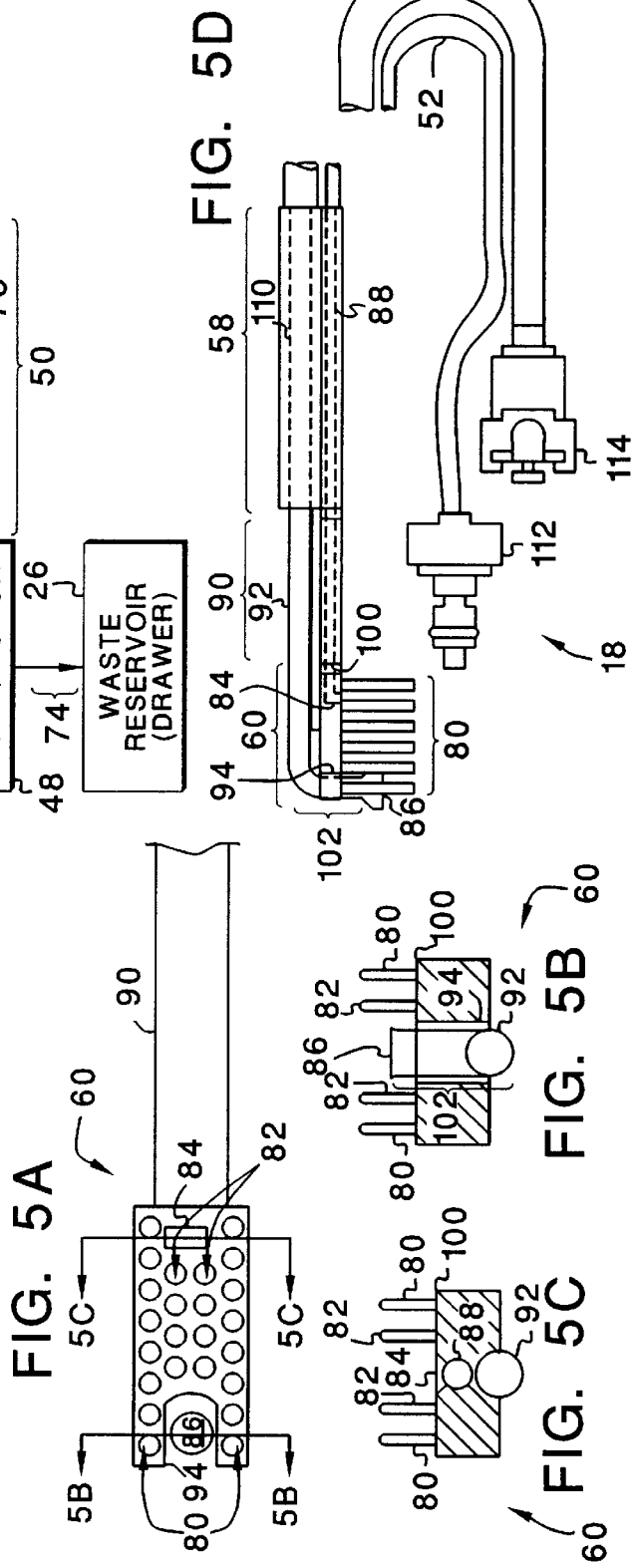

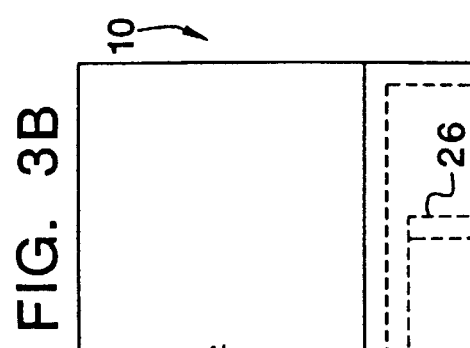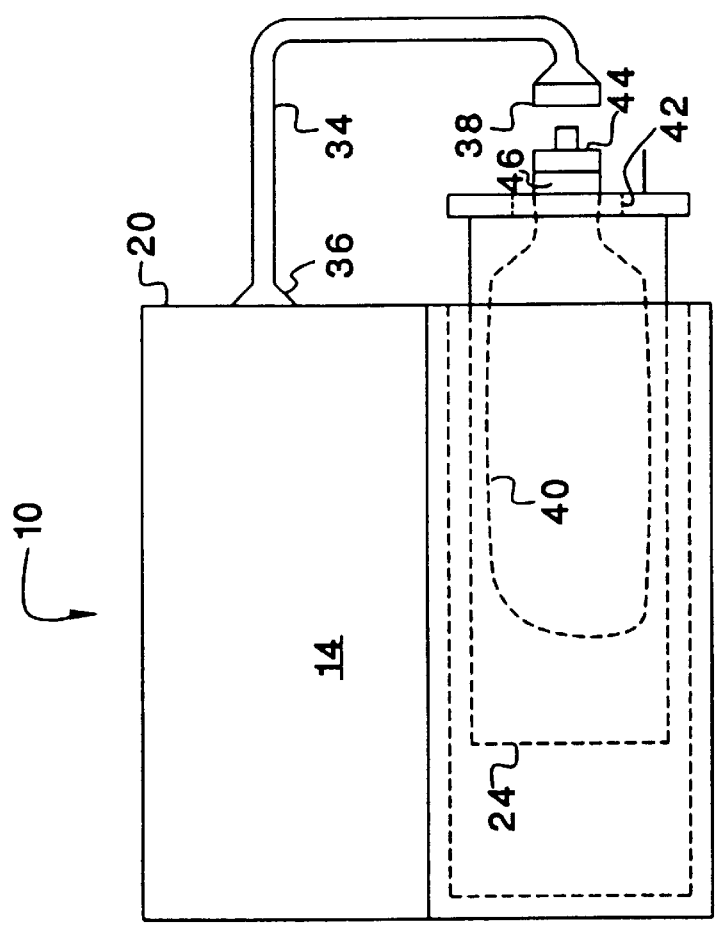

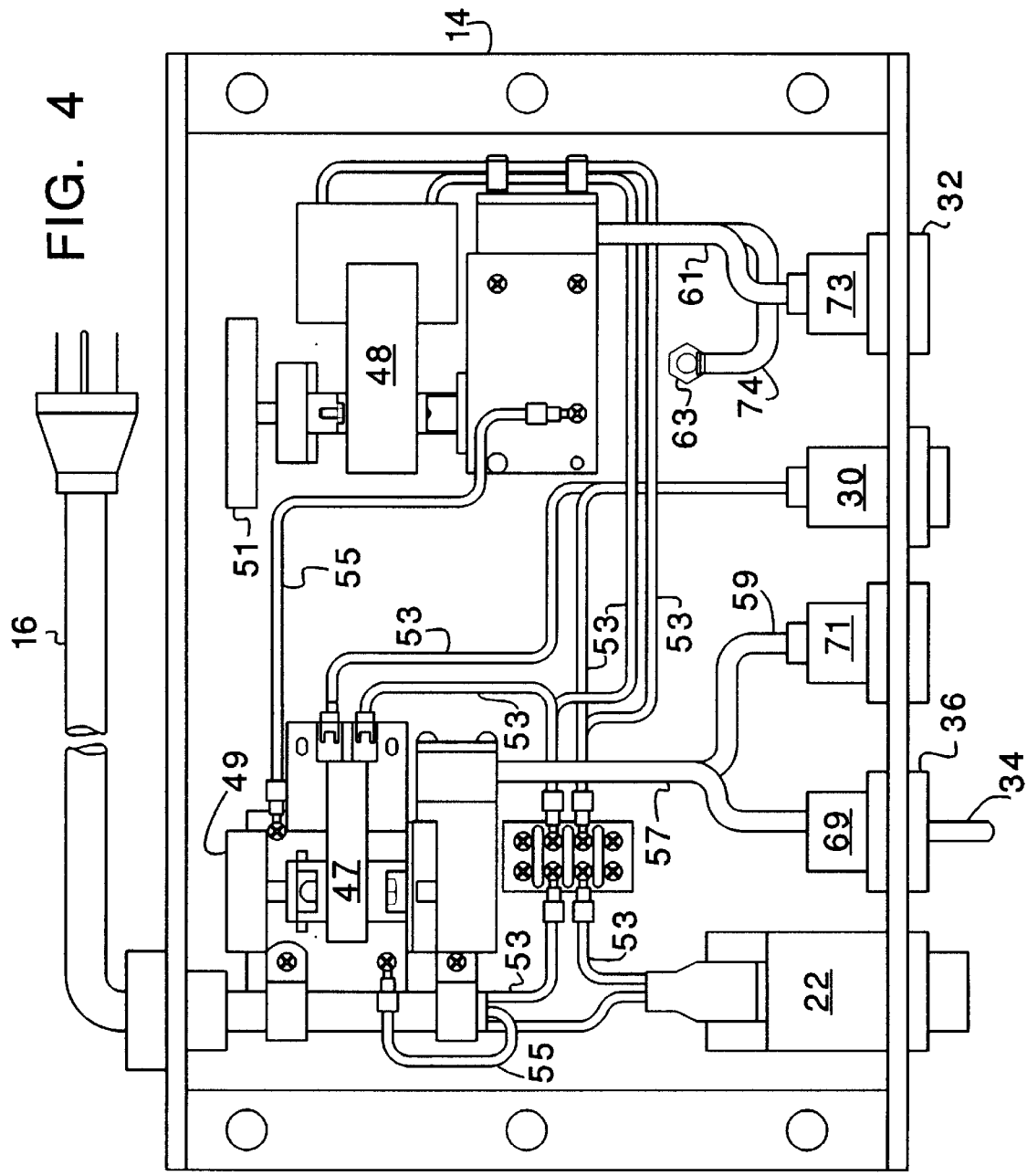

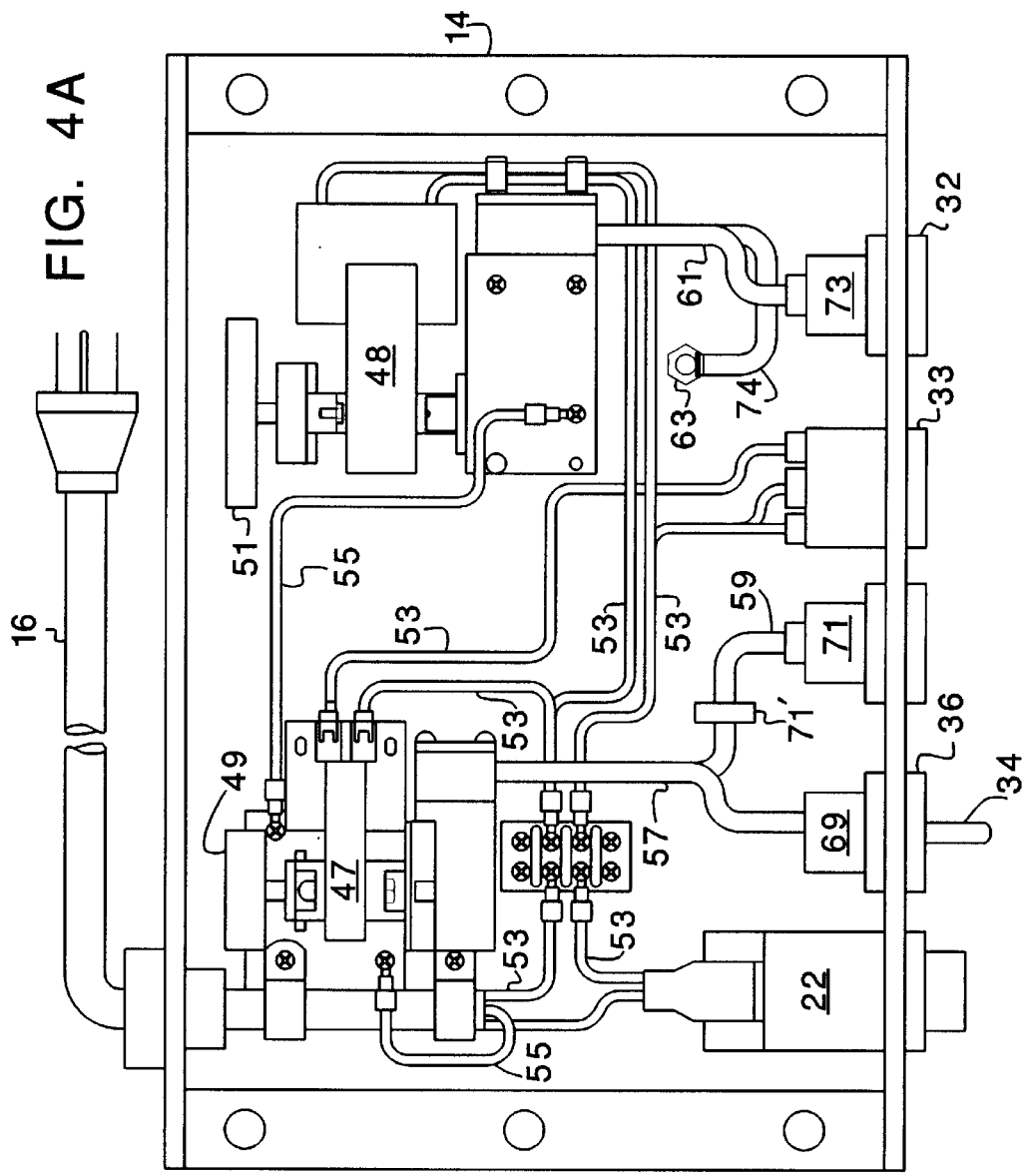

LIQUID DENTAL CLEANING SOLUTION

This is a Continuation-in-Part application of U.S. patent application Ser. No. 08/476,205, filed Jun. 7, 1995, for IMPROVED DENTAL HYGIENE DEVICE AND CLEANING SOLUTION, incorporated herein by reference, now abandoned, which is a Continuation-in-Part application of U.S. patent application Ser. No. 08/259,917, now U.S. Pat. No. 5,573,398, filed Jun. 10, 1994, for DENTAL HYGIENE DEVICE AND CLEANING SOLUTION, incorporated herein by reference.

BACKGROUND OF THE INVENTION

The present invention relates to dental hygiene, and more particularly to the cleaning of teeth in humans and other animals. Even more particularly, the present invention relates to a cleaning solution for cleaning human or other animal teeth.

The practice of oral hygiene in hospitals, skilled nursing facilities, home health care and the like has always been a rather vague and ill defined procedure. Some people in such institutions are, of course, able to care for themselves by using conventional tooth brushes and commercially available oral hygiene products such as toothpaste, mouth washes, and the like. However, others both in and out of such institutions are largely or totally dependent on others. For example, people suffering from arthritis, stroke victims, and other medically compromised people, may find it difficult to hold and manipulate a tooth brush while other more severely ill people, such as senile or comatose patients, simply cannot maintain their own oral hygiene programs.

Those people who find it difficult to hold and manipulate a conventional tooth brush are very often ineffective when it comes to accomplishing adequate oral hygiene. Similarly, those attempting to help the people who are unable to help themselves, such as the staff personnel of a hospital or nursing home, or the family of such a person, are not trained in the techniques needed for administering proper oral hygiene to others. And, it is very awkward, messy, and otherwise difficult for untrained medical or lay people to help others with the needed oral hygiene. As a result, very often even in medical institutions, the practice of oral hygiene is inadequate and in some cases, non-existent.

Thus, what is needed is a portable device for cleaning human or other animal teeth, that can be easily utilized by untrained medical personnel in a variety of settings, including in health care facilities, rest homes, or residences.

In addition to the needs for a device that can be used for cleaning teeth, there is a need for a dental hygiene material that is suitable for use with such device or as an oral rinse that can be used in lieu of conventional tooth cleaning pastes (toothpaste). Unfortunately, the relatively thick toothpastes that are commonly available for dental hygiene are difficult for some people in hospitals, skilled nursing facilities and home health care to apply. Furthermore, such pastes are difficult for such people to expel after having performed oral hygiene. In addition, such pastes, unless applied carefully, may not be applied throughout a person's mouth and therefore complete cleaning may not occur, especially disabled individuals and children. Thus, a dental hygiene material that is in a liquid form that can be easily and automatically irrigated into a person's mouth and simultaneously suctioned away, while still providing for plaque and debris removal, and for breath freshening, would be advantageous, and would be especially advantageous if such dental hygiene solution can also be used as an oral rinse in lieu of conventional toothpaste.

The present invention advantageously addresses the above and other needs.

SUMMARY OF THE INVENTION

The present invention addresses the needs above as well as other needs by providing a cleaning solution for cleaning human or other animal teeth.

The present invention can be characterized as a dental hygiene solution that includes (a) an aqueous solution of sodium fluoride in water having from between about 0.25 ppm and about 8 ppm sodium fluoride, e.g., from between about 0.25 ppm and about 1 ppm, e.g., about 0.5 ppm; (b) sodium tripolyphosphates from 100 to 1000 mg per gallon water, e.g., from between about 100 mg and about 600 mg per gallon, e.g., 200 mg per gallon; (c) disodium edetate from between about 0.01 cc and 0.5 cc per gallon water, e.g., from between about 0.01 cc and 0.13 cc per gallon, e.g., 0.051 cc per gallon; and (d) a detergent, e.g., NEUTRONYX-656 (nonyl phenol) (available from Stepan Company of Illinois) from between about 1 and 10 cc per gallon of water, e.g., from about 2 to 8 cc per gallon, e.g., about 3 cc per gallon.

It is thus a feature of the invention to provide a dental hygiene solution suitable for use in the dental hygiene device described herein or alternatively as an oral rinse suitable for use in lieu of conventional toothpastes.

BRIEF DESCRIPTION OF THE DRAWINGS

The above and other aspects, features and advantages of the present invention will be more apparent from the following more particular description thereof, presented in conjunction with the following drawings wherein:

FIG. 2 shows a block diagram of the dental hygiene device of FIGS. 1 and 1A;

FIG. 3A shows a side view of the control unit of the dental hygiene device of FIGS. 1 and 1A that depicts how a supply drawer thereof is slidably opened to allow replacement of a supply bladder;

FIG. 3B shows another side view of the dental hygiene device of FIGS. 1 and 1A that depicts a waste drawer thereof;

FIG. 4 shows a top view of the dental hygiene device of FIG. 1 with an upper plate removed to expose the components therein;

FIG. 4A shows a top view of the dental hygiene device of FIG. 1A with an upper plate removed to expose the components therein;

FIG. 5A shows a top view of a brush head of the brush assembly of the dental hygiene device of FIG. 1 and FIG. 1A FIG. 5B shows a cross-sectional view of the brush head taken along line 5B—5B of FIG. 5A;

FIG. 5C shows cross-sectional view of the brush head 60 taken along line 5C—5C of FIG. 5A; and FIG. 5D shows a side view of the brush head of the brush assembly;

Corresponding reference characters indicate corresponding components throughout the several views of the drawings.

DETAILED DESCRIPTION OF THE INVENTION

The following description is of the presently contemplated best mode of practicing the invention. This description is not to be taken in a limiting sense, but is made merely for the purpose of describing the general principles of the invention. The scope of the invention should be determined with reference to the claims.

Figure 1:
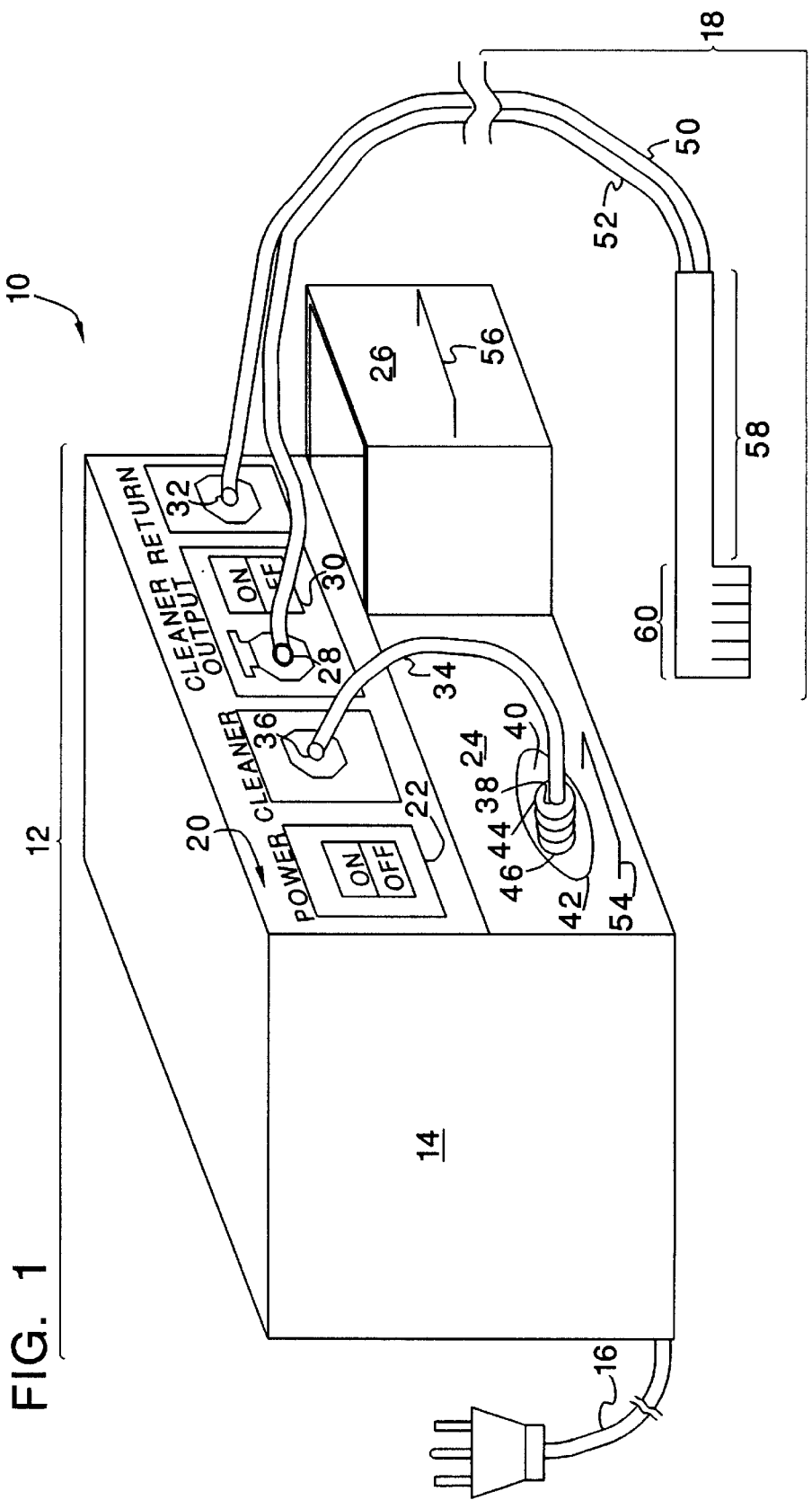
FIG. 1 shows a perspective view of a dental hygiene device made in accordance with the present invention, including a control unit, detachable brush assembly, and power cord.

Referring first to FIG. 1, a perspective view is shown of a dental hygiene device 10 made in accordance with the present invention. The dental hygiene device 10 includes a control unit 12 housed in a housing 14, a power cord 16, and an irrigation/suction brush assembly 18. The control unit 12 has a control panel 20 that includes a main power switch 22, a supply reservoir drawer 24, a waste reservoir drawer 26, an irrigation outlet 28, an irrigation pump switch 30, a suction inlet 32, and a supply tube 34.

The supply tube 34 is coupled at one end 36 to the control panel 20 and at the other end 38 to a collapsible supply bladder 40 that protrudes through an opening 42 in the supply reservoir drawer 24. Preferably, the supply tube 34 is detachably coupled to the supply bladder 40 at a cap 44 of the supply bladder 40, which cap 44 protrudes through the opening 42 in the supply reservoir drawer 24. The cap 44 is a threaded cap that screws onto a cap opening 46 on the supply bladder 40, as is known in the art. The supply bladder 40 is preferably a flexible, disposable, plastic bladder bag. The supply bladder 40 is housed in the supply reservoir drawer 24 with its cap opening 46 protruding through the opening 42 in the supply reservoir drawer 24.

The irrigation/suction brush assembly 18 is detachably coupled to the control panel 20 by a suction tube 50 at the suction inlet 32, and by an irrigation tube 52 at the irrigation outlet 28. The irrigation/suction brush assembly 18 also includes a handle 58 and a brush head 60, as explained more completely below.

Figure 1A:
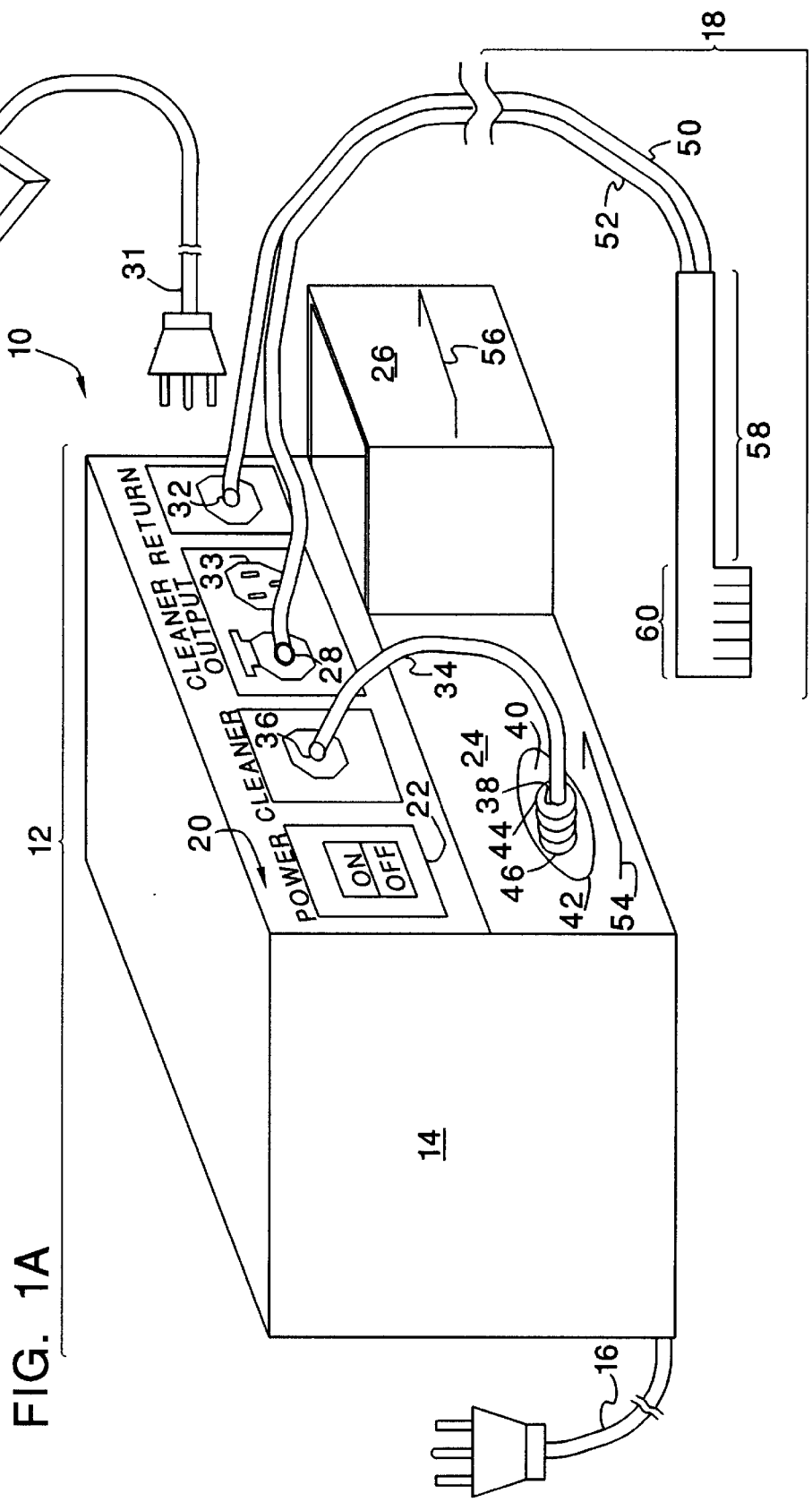
FIG. 1A shows another embodiment of a dental hygiene device made in accordance with the present invention.

The master power switch 22 is used to control whether power received through the power cord 16 is applied to the dental hygiene device 10. The irrigation pump switch 30 is used in combination with the master power switch 22 to control whether such power is also supplied to an irrigation pump (not shown in FIG. 1) within the housing 14, and thereby to control whether a dental hygiene solution is pumped into the irrigation tube 52 through the irrigation/suction brush assembly 18. Preferably, the irrigation pump switch 30 is a footswitch 30' (FIG. 1A) that is remotely located from the housing 14. The foot-switch 30' is of conventional design, and therefore further description is not made herein. An electrical cord 31, is used to couple the foot-switch to the dental hygiene device 10, and is preferably detachable from the dental hygiene device 10 at an electrical connector 33 located on the control panel 20 of the housing 14. A perspective view is shown in FIG. 1A of a dental hygiene device 10 having the electrical cord 31, connector 33, and foot-switch 30'.

The dental hygiene solution, in one embodiment, may be an aqueous solution of sodium fluoride, having from 0.5 to 1.0, e.g., 0.850, milligrams sodium fluoride per fluid ounce of distilled water. The dental hygiene solution may also include ascorbic acid from 350 to 425, e.g., 392.2, times the sodium fluoride concentration; bioflavinoids from 3 to 4.5, e.g., 3.922 times the sodium fluoride concentration; calcium ascorbate from 19 to 20, e.g., 19.61, times the sodium fluoride concentration; magnesium ascorbate from 9 to 10.5, e.g., 9.804, times the sodium fluoride concentration; and potassium ascorbate from 19 to 20, e.g., 19.41 times the sodium fluoride concentration. The dental hygiene solution also may include a flavoring agent such as those flavoring agents commonly used in the art.

An example composition of a dental hygiene solution made in accordance with the present invention, which may be adjusted to the quantity of the fluid being mixed, comprises:

| | |
|---|---|
| Distilled Water | 6 ounces |
| Vitamin C | 2000 mg |
| Bioflavinoids | 20 mg |
| Calcium Ascorbate | 100 mg |
| Magnesium Ascorbate | 50 mg |
| Potassium Ascorbate | 99 mg |
| Flavoring Agent | 2 drops |
| Sodium Fluoride | 4 drops (each drop contains 1.275 mg of Sodium Fluoride which is equivalent to .125 mg Fluoride ion.) |

An alternative, and preferred, dental hygiene solution is an aqueous solution of sodium fluoride U.S.P./N.F., having from between 0.25 ppm to 8 ppm, sodium fluoride, e.g., about 0.25 ppm and 1 ppm, e.g., about 0.5 ppm sodium fluoride. The water may be purified water, such as is achieved using a reverse osmosis water purification system, or may be distilled water. The preferred dental hygiene solution also includes sodium tripolyphosphates F.C.C. from 100 to 1000 mg, e.g., from between about 100 mg and 600 mg, e.g., 200 mg, per gallon of water; and disodium edetate U.S.P./N.F. from 0.01 cc to 0.5 cc, e.g., from between about 0.01 cc and 0.13 cc, e.g., about 0.051 cc per gallon of water. The preferred dental hygiene solution further includes a detergent, such as NEUTRONYX-656 (nonyl phenol) (available from Stepan Company of Illinois) from 1 to 10 cc, e.g., from between about 2 cc and 8 cc, e.g., about 3 cc per gallon of water. The preferred dental hygiene solution further includes rectified F.C.C. oil of spearmint from 1 to 5 cc, e.g., 2 cc, per gallon of water; natural F.C.C. oil of peppermint from 1 to 5 cc, e.g., 2 cc, per gallon of water; DL-menthol crystal U.S.P./N.F. from 500 to 1500 mg, e.g., 750 mg, per gallon of water; natural glycerin U.S.P./N.F. from 1 to 8 cc, e.g., 1.6 cc, per gallon of water; 99% isopropyl alcohol U.S.P./N.F. from 10 cc to 60 cc, e.g., 15 cc, per gallon of water; calcium ascorbate dihydrate F.C.C. from 200 to 1000 mg, e.g., 400 mg, per gallon of water; EQUAL (Nutrasweet), which is a common brand-name sweetener (or an equivalent sweetening agent) from 10 to 35 g, e.g., 20 g per gallon of water; blue coloring F.D. and C. #1 (or an equivalent coloring agent) from 2 to 5 drops, e.g., 3 drops per gallon of water; and sodium carbonate U.S.P./N.F. to adjust the pH to about 7.0.

An example composition of the preferred dental hygiene solution, which may be adjusted to the quantity of fluid being mixed, comprises the following ingredients, which are preferably U.S. pharmaceutical grade:

| | |
|---|---|
| Water (purified) | 1 Gallon (approx. 3785 ml) |
| Isopropyl Alcohol U.S.P./N.F. | 15 cc |
| Rectified F.C.C. Oil of Spearmint | 2 cc |
| Natural F.C.C. Oil of Peppermint | 2 cc |
| DL-Menthol Crystal U.S.P./N.F. | 750 mg |
| Calcium Ascorbate | 400 mg |

-continued

| | |
|---|---|
| Dihydrate F.C.C. | |
| NEUTRONYX-656 | 3 cc |
| (nonyl phenol) | |
| Natural Glycerin | 6 cc |
| U.S.P./N.F. | |
| Sodium Fluoride | 8 drops (0.24 mg per drop) |
| U.S.P./N.F. | |
| Sodium | 200 mg |
| Tripolyphosphates | |
| F.C.C. | |
| Disodium Edetate | 12 drops (0.0043 ml per drop) |
| U.S.P./N.F. | |
| EQUAL (Nutrasweet) | 20 g |
| Blue Coloring F.D. | 3 drops (0.123 ml per drop) |
| and C. #1 | |
| Sodium Carbonate | to adjust pH to 7.0 |
| U.S.P./N.F. | |

The example composition of preferred dental hygiene solution may be prepared in accordance with the following method:

(a) Heat the water to approximately 150° F. (65.56° C.);

(b) Dissolve oil of spearmint, oil of peppermint, menthol and glycerin in the alcohol, and, while stirring, add mixture into the heated water;

(c) Dissolve calcium ascorbate into the heated water;

(d) Dissolve NEUTRONYX-656 into the heated water;

(e) Add sodium fluoride into the heated water;

(f) Dissolve sodium tripolyphosphates into the heated water;

(f) Add disodium edetate into the heated water;

(h) Add EQUAL to the heated water;

(i) Add blue color to the heated water;

(j) Add sodium carbonate q.s. to adjust pH to 7.0; and (k) Stir the entire mixture, and filter the mixture with 615–20 filter paper.

The waste reservoir drawer 26 is preferably removable so that it can be easily removed and emptied as needed. The waste reservoir drawer 26 is filled by a suction pump (not shown in FIG. 1) within the housing 14, which suctions the dental hygiene solution from the suction tube 50 and expels it into the waste reservoir drawer 26.

The supply reservoir drawer 24 is also preferably removable so that it can be easily removed when the supply bladder 40 needs to be replaced. A fresh supply bladder can easily be inserted into the supply reservoir drawer 24. Preferably, sealed supply bladders containing the dental hygiene solution as described above may be prepared and sold as a supply component of the device 10. Thus, users of the device 10 need only purchase or otherwise acquire the control unit 12, and then purchase one or more supply bladders, filled with the dental hygiene solution as required. Both the supply reservoir drawer 24 and the waste reservoir drawer 26 have handles 54,56, respectively, to facilitate their opening and closing.

Referring next to FIG. 2, a block diagram is shown of a dental hygiene device 10 made in accordance with the present invention. The power cord 16 is shown coupled to the master power switch 22, which preferably includes a circuit breaker. Also shown are the irrigation pump switch 30, the irrigation pump/motor 47, the supply reservoir 40 (or supply bladder 40), the suction pump/motor 47, the waste reservoir 26 (or waste reservoir drawer 26), the irrigation/suction brush 18, an irrigation valve/irrigation check valve 71, a supply valve/supply check valve 69, and a suction valve/suction check valve 73.

The master power switch 22, through suitable electrical connections, e.g., wires and/or printed circuit boards, provides power from the power cord 16 to the irrigation pump switch 30 and to the suction pump/motor 48. The irrigation pump switch 30 supplies, through suitable electrical connections, power to the irrigation pump/motor 47.

The supply reservoir 40 is coupled to the irrigation pump/motor 47 through the supply tube 34, and supplies the dental hygiene solution to the irrigation pump/motor 47. The irrigation pump/motor 47 is coupled to the irrigation/suction brush assembly 18 via the irrigation tube 52.

The waste reservoir 26 receives spent (waste) dental hygiene solution from the suction pump/motor 48 via a waste tube 74. The suction pump/motor 48 draws the spent dental hygiene solution through the suction tube 50 from the irrigation/suction brush assembly 18.

In operation, when power is supplied to the dental hygiene device 10 through the power cord 16 and master power switch 22, the suction pump/motor 48 draws spent dental hygiene solution through the suction tube 50 from the irrigation/suction brush assembly 18.

Similarly, when the power is applied through the power cord 16 and the master power switch 22, and the irrigation pump switch 30 (or the foot switch 30') is placed into an "on" position, the irrigation pump/motor 47 pumps dental hygiene solution from the supply reservoir 40 through the irrigation tube 52 and into the irrigation/suction brush assembly 18. Advantageously, in the event that excessive dental hygiene solution is being supplied to the irrigation/suction brush assembly 18, the irrigation pump switch 30 (or the foot switch 30') can be switched into an "off" position thereby terminating the supply of power to the irrigation pump/motor 47 and consequently terminating the pumping of the dental hygiene solution through the irrigation tube 52.

The irrigation/suction brush assembly 18 is detachably connected to the control unit 12 via the check valves 71,73. This detachability advantageously allows several patients, each having his or her own brush assembly 18, to share the same control unit 12.

The supply valve/supply check valve 69 serves two functions. The first function is to close off the supply tube 34 when it is detached from the supply reservoir 40, so that dental hygiene solution in the supply tube 43 does not spill when the supply tube 34 is detached. The second function is to prevent the reverse flow of the dental hygiene solution into the supply reservoir 40 from the supply tube 34, and thereby to prevent contamination of the dental hygiene solution in the supply reservoir 40.

The irrigation valve/irrigation check valve 71 also serves a function similar to those of the supply valve/supply check valve 69: the irrigation valve/irrigation check valve 71 closes off the irrigation tube 52 and the irrigation outlet 28 when the irrigation tube 52 is detached from the irrigation outlet 28, so as to prevent spillage of the dental hygiene solution from the irrigation tube 52 and the irrigation outlet 28. A separate check valve 71' (FIG. 4A) prevents the reverse flow of the dental hygiene solution from the irrigation tube 52 into the irrigation outlet 28, and therefore the contamination of the dental hygiene solution in the irrigation outlet 28, irrigation pump/motor 47, and supply tube 34.

Note that both the supply valve/supply check valve 69, and the irrigation valve/irrigation check valve 71 include at least two integrated valve connectors, one that is coupled to the control panel and another that is coupled to the supply or irrigation tube 34 or 52, respectively. In operation, the two integrated valve connectors are detachably coupled to one another so as to provide for easy detachment of the irrigation/suction brush assembly 18 or supply bladder 40, respectively.

The suction valve/suction check valve 73 also performs two analogous functions. That is, it closes off the suction tube 50 when the suction tube is removed from the suction inlet 32. However, the suction valve/suction check valve 73 will preferably not close off the suction inlet 32 when the suction tube 50 is removed so as to prevent damage to the suction pump/motor 48 in the event the suction pump/motor 48 is operated with the suction tube 50 removed. The suction valve/suction check valve 73 also prevents the reverse flow of the dental hygiene solution from the suction inlet 32 into the suction tube 50, and thereby prevents contamination of the dental hygiene solution in the suction tube 50 with the dental hygiene solution in the suction inlet 32 and suction pump/motor 48.

Note that the suction valve/suction check valve 73 includes an integrated valve connector, and a valve-less connector. The valve-less connector is coupled to the control panel and the integrated valve connector is coupled to the suction tube 50. In operation, the valve-less connector and the integrated valve connector are detachably coupled to one another so as to provide for easy detachment of the irrigation/suction assembly 18.

A suitable irrigation valve/irrigation check valve 71, supply valve/supply check valve 69, and suction valve/suction check valve 73 are available as part no's 69-BUH 22-02, 71-PMCD 16-02 and 73-PMC 42-03 from Colder Products Company of Saint Paul, Minn. A suitable separate check valve 71' (FIG. 4A) is available as part No. S5401001N from Burron, OEM Division, of Pennsylvania.

Note that the irrigation valve/irrigation check valve 71, the supply valve/supply check valve 69, and the suction valve/suction check valve 73 are preferably purely mechanical valves, however, they may be automatic solenoid activated valves operated and/or monitored electrically via respective control lines 75.

In this way, dental hygiene solution is simultaneously and automatically supplied to and suctioned from the irrigation/suction brush assembly 18, without the need for the person using the dental hygiene device 10 to manually expel thick dental hygiene paste (e.g., toothpaste).

Referring next to FIG. 3A, a side view is shown of the dental hygiene device 10, and in particular, of the housing 14, the supply reservoir drawer 24, the supply bladder 40, the cap opening 46, the cap 44 and the supply tube 34. As can be seen, the supply tube 34 is attached at one end 36 to the control panel 20 and can be detachably attached to the cap 44 of the supply bladder 40 at the other end 38. The cap 44 and the cap opening 46 of the supply bladder 40 protrude through the opening 42 of the supply drawer 24 to facilitate attachment of the supply tube 34 to the cap 44.

Referring next to FIG. 3B, a side view of the opposite side of the dental hygiene device 10 is shown, and in particular, of the housing 14 and the waste drawer 26 (or the waste reservoir 26). As illustrated, the waste reservoir 26 is slideably removable from the housing 14 so that when the waste drawer 26 becomes full of spent dental hygiene solution, it can be removed from the housing 14 and emptied. Preferably the housing 14 and the waste drawer 26 are made, at least in part, from a transparent material, such as plexiglass, or other clear plastic, so that it can easily be determined through visual inspection whether the waste drawer 26 needs to be emptied.

Also shown in FIG. 3B is a fitting 63 through which the spent dental hygiene solution flows into the waste reservoir. The fitting 63 is described more completely hereinbelow.

Referring next to FIG. 4, a top view of the dental hygiene device 10 is shown with an upper panel removed to depict the arrangement of the components used therein. The power cord 16, the housing 14 and the master power switch 22 are shown, along with the irrigation pump/motor 47, the supply tube 34, the irrigation outlet 28, the irrigation pump switch 30, the suction pump/motor 48, the suction inlet 32, and the waste tube 74. In the embodiment of FIG. 4A, the electrical connector 33 is shown instead of the irrigation pump switch 30. Also shown are an irrigation pump/motor cooling fan 49, a suction pump/motor cooling fan 51, power supply wires 53, grounding wires 55, a supply pump tube 57, an irrigation pump tube 59, and a suction pump tube 61. The irrigation valve/irrigation check valve 71, and the suction valve/suction check valve 73 are also shown. In the embodiment of FIG. 4A, the separate check valve 71' is also shown.

A suitable irrigation pump/motor 47 is available as part no. 5002F-000-FP from ASF Inc. of Norcross, Ga. A suitable suction pump/motor 48 is available as part no. 8010-000-QP from ASF Inc. of Norcross, Ga.

Power is received into the housing 14 via the power cord 16. Power supply wires 53 carry the power to the master power switch 22, the suction pump/motor 48, and the irrigation pump switch 30. The irrigation pump switch 30 carries the power to the irrigation pump/motor 47. When the master power switch 22 is turned on, the suction pump/motor 48 operates, and power is supplied to the irrigation pump switch 30 (or the foot switch 30'). When both the master power switch 22 and the irrigation pump switch 30 (or the foot switch 30') are turned on, the irrigation pump/motor 47 operates. Hence, it is not possible for the irrigation pump/motor 47 to be turned on when the suction pump is turned off.

When operating, the irrigation pump/motor 47 pumps the dental hygiene solution from the supply tube 34 into the supply pump tube 57, through the irrigation pump/motor 47, and out the irrigation pump tube 59 to the irrigation outlet 71. Similarly, when the suction pump/motor 48 operates, the dental hygiene solution is pumped in through the suction inlet 32 into the suction pump tube 61, through the suction pump/motor 48 and out the waste tube. The waste tube 74 is coupled to the fitting 63 that is positioned above the waste reservoir 26 (FIG. 3B). The dental hygiene solution flows from the fitting 63 into the waste reservoir 26 by gravity.

An example of the dental hygiene device has the following dimensions and components:

| | |
|---|---|
| Plastic housing (Control unit) | 6" H, 8 1/8" W, 6 1/4" D |
| Supply tube (plastic) | .125" ID, .250" OD |
| Irrigation tube (plastic) | .125" ID, .250" OD |
| Suction tube (plastic) | .187" ID, .300" OD |
| Supply reservoir drawer | 2 9/16" H, 5 1/2" W, 5 15/16" D |
| Waste reservoir drawer | 2 9/16" H, 2" W, 5 15/16" D |
| Approximate weight (Control unit) | 10 LBS |

Referring next to FIGS. 5A, 5B and 5C, details of the brush head 60 are shown. At least two, and preferably at least four, parallel rows of bristles 80,82 protrude from the bottom of the brush head (normal to the plane of the paper as oriented in FIG. 5A). An irrigation port 84 consists of a slot that is interposed between the outermost two rows of bristles 80 at one end of the rows 80. The slot of the irrigation port 84 is perpendicular to the rows 80. The irrigation port 84 is in fluid communication with an irrigation conduit 88 that is longitudinally within a shaft 90 that is substantially parallel to the rows 80 and attaches the brush head 60 to the handle 58.

A suction port 86, circular in cross section, is interposed between the outermost two rows of bristles 80 at another end of the bristle rows 80. The suction port 86 is coupled to a suction connector 92 that passes outside the shaft 90 and connects to a suction conduit in the handle 58. Unlike the irrigation port 84, which is integral with the brush head 60, the suction port 86 lies in a channel 94 that is formed in the end of the brush head 60 furthest from the shaft 90.

In operation, dental hygiene solution is ejected through the irrigation port 84 under pressure generated by the irrigation pump/motor 47 (FIG. 2). At the same time, spent dental hygiene solution and other debris that are loosened from teeth by the bristles 80,82 and dental hygiene solution are drawn into the suction port 86 by suction that is created by the suction pump/motor 48.

As seen best in FIG. 5B, the bristles 80 protrude from a surface 100 of the brush head 60. The suction nozzle 102 is coupled at one end to the suction port 86 and is coupled at another end to the suction connector 92, as explained more completely below. The suction nozzle 102 protrudes from the surface 100 about half the distance that the outermost two rows of bristles 80 protrude. The bristles 80, 82 protrude out from the surface 100 a distance of about 0.375 in.

As seen best in FIG. 5, the relative location of the suction connector 92 and the irrigation conduit 88 are shown within the brush head 60. The irrigation port 84 is formed in the brush head 60 by, e.g., machining the brush head 60, which is preferably made from resin or plastic.

Referring next to FIG. 5D, a side view is shown of the irrigation/suction brush 18. The bristles 80 protrude from the surface 100 of the brush head 60, and the suction port 86 and suction nozzle 102 are shown protruding through the channel 94 in the brush head 60. As can be seen, the suction nozzle 102 preferably protrudes about half (50%) as far as the outermost two rows of bristles 80 protrude, although the suction nozzle 102 may protrude one quarter (25%) as far as the outermost two rows of bristles 80 protrude. It is important that an adequate space be provided between a tip of the suction nozzle 102 and the end of the bristles 80 so that the suction nozzle 102 cannot easily be forced against the gums or teeth, and thus blocked from preforming its suction function. At the same time, it is important that the suction nozzle protrude from the surface 100 so that it is positioned close to the gums and teeth so as to facilitate suctioning of the dental hygiene solution and debris. The suction nozzle 102 is integrally coupled to the suction connector 92, which is coupled to the suction conduit 110 that passes longitudinally through the handle 58. The suction conduit 110 is also coupled to the suction tube 50.

Also shown in FIG. 5D is the irrigation port 84 that is coupled to the irrigation conduit 88. The irrigation conduit 88 passes longitudinally through the shaft 90 and the handle 58, and is coupled to the irrigation tube 52. The portion of the irrigation conduit 88 that passes through the shaft 90 and the brush head 60 is also referred to herein as the irrigation duct in order to distinguish it from the irrigation conduit 88, which passes through the handle 58.

In practice, the irrigation tube 52 and suction tube 50 are preferably about six feet long, and are detachably coupled to the irrigation outlet 28 and suction inlet 32, respectively, of the control unit 12. Detachable couplings 112, 114 couple the irrigation tube 52 and the suction tube 50 to the irrigation outlet 28 and suction inlet 32, respectively. The coupling 112 includes one of the integrated valve connectors that are included in the irrigation valve/irrigation check valve 71 and is available as part no. PMCD 16-02 from Colder Products Company of Saint Paul, Minn. The coupling 114 includes the integrated valve connections that is included in the suction valve/suction check valve 73 and is available as part no. PMCD 42-01 from Colder Products Company of Saint Paul, Minn.

The size and weight of the control unit 12 make it possible for the entire device 10 to be readily portable. That is, the device can be easily carried to those in need of dental hygiene, particularly those who may be bed-ridden or are otherwise unable to receive or provide themselves with needed dental hygiene care.

Thus, it is seen that the invention provides an improved dental hygiene device that provides for simultaneous irrigation and suction through an irrigation/suction brush.

It is also seen that the invention provides an improved dental hygiene solution suitable for use with the dental hygiene device described herein.

While the invention herein disclosed has been described by means of specific embodiments and applications thereof, numerous modifications and variations could be made thereto by those skilled in the art without departing from the scope of the invention set forth in the claims.

What is claimed is:

1. A dental hygiene solution that includes:

water;

sodium tripolyphosphates from 100 to 1000 mg per gallon of water;

disodium edetate from 0.01 cc to 0.5 cc per gallon of water; and a detergent from 1 to 10 cc per gallon of water.

2. The dental hygiene solution of claim 1 including:

oil of spearmint from 1 to 5 cc per gallon of water.

3. The dental hygiene solution of claim 1 including:

oil of peppermint from 1 to 5 cc per gallon of water.

4. The dental hygiene solution of claim 1 including:

menthol from 500 to 1500 mg per gallon of water.

5. The dental hygiene solution of claim 1 including:

glycerine from 1 to 8 cc per gallon of water.

6. The dental hygiene solution of claim 1 including:

calcium ascorbate from 200 to 1000 mg per gallon of water.

7. The dental hygiene solution of claim 1 including:

a sweetening agent from 10 to 35 g per gallon of water; and a coloring agent from 2 to 5 drops per gallon of water.

8. The dental hygiene solution of claim 1 including:

oil of spearmint from 1 to 5 cc per gallon of water;

oil of peppermint from 1 to 5 cc per gallon water;

menthol from 500 to 1500 mg per gallon of water;

glycerine from 1 to 8 cc per gallon of water; and alcohol from 10 to 60 cc per gallon.

9. The dental hygiene solution of claim 8 including:

calcium ascorbate from 200 to 1000 mg per gallon of water.

10. The dental hygiene solution of claim 9 including:

a sweetening agent from 10 to 35 g per gallon of water; and a coloring agent from 2 to 5 drops per gallon of water.

11. The dental hygiene solution of claim 10 wherein:

said water is an aqueous solution of 1.89 milligrams sodium fluoride per gallon of water;

sodium tripolyphosphates are 200 mg per gallon of water;

disodium edetate is 0.128 cc per gallon of water; and detergent is 3 cc per gallon of water.

12. The dental hygiene solution of claim 1 including sodium fluoride from 0.25 to 8 ppm.

13. A dental hygiene solution that includes:

water;

sodium tripolyphosphates from 100 to 1000 mg per gallon of water;

disodium edetate from 0.01 ml to 0.5 ml per gallon of water; and a detergent from 1 to 10 cc per gallon of water.

14. The dental hygiene solution of claim 13 including:

oil of spearmint from 1 to 5 cc per gallon of water.

15. The dental hygiene solution of claim 13 including:

oil of peppermint from 1 to 5 cc per gallon of water.

16. The dental hygiene solution of claim 13 including:

menthol from 500 to 1500 mg per gallon of water.

17. The dental hygiene solution of claim 13 including:

glycerine from 1 to 5 cc per gallon of water.

18. The dental hygiene solution of claim 13 including:

calcium ascorbate from 200 to 800 mg per gallon of water.

19. The dental hygiene solution of claim 13 including:

a sweetening agent from 20 to 35 g per gallon of water; and a coloring agent from 0.15 to 0.5 ml per gallon of water.

20. The dental hygiene solution of claim 13 including:

oil of spearmint from 1 to 5 cc per gallon of water;

oil of peppermint from 1 to 5 cc per gallon water;

menthol from 500 to 1500 mg per gallon of water;

glycerine from 1 to 5 cc per gallon of water; and ethyl alcohol from 20 to 60 ml per gallon.

21. The dental hygiene solution of claim 20 including:

calcium ascorbate from 200 to 800 mg per gallon of water.

22. The dental hygiene solution of claim 19 including:

a sweetening agent from 20 to 35 g per gallon of water; and a coloring agent from 0.15 to 0.5 ml per gallon of water.

23. The dental hygiene solution of claim 22 wherein:

said water is an aqueous solution of 1.89 milligrams sodium fluoride per gallon of water;

sodium tripolyphosphates are 200 mg per gallon of water;

disodium edetate is 0.051 ml per gallon of water; and detergent is 3 cc per gallon of water.

24. The dental hygiene solution of claim 13 including sodium fluoride from 0.25 to 8 ppm.

* * * * *